United States Patent
Sidewell et al.

(10) Patent No.: US 6,818,456 B2
(45) Date of Patent: Nov. 16, 2004

(54) COLOR CONTRAST SYSTEM FOR LATERAL FLOW IMMUNOASSAY TESTS

(75) Inventors: Steven P. Sidewell, Dana Point, CA (US); Steven S. Bachand, Laguna Niguel, CA (US)

(73) Assignee: Varian, Inc., Palo Alto, CA (US)

(*) Notice: Subject to any disclaimer, the term of this patent is extended or adjusted under 35 U.S.C. 154(b) by 370 days.

(21) Appl. No.: 09/910,198

(22) Filed: Jul. 20, 2001

(65) Prior Publication Data

US 2003/0017615 A1 Jan. 23, 2003

(51) Int. Cl.$^7$ .............................................. G01N 33/53
(52) U.S. Cl. ...................... 436/518; 435/7.1; 435/7.94; 435/287.7; 435/970; 436/514; 436/530; 436/541; 436/161; 436/16; 436/810; 436/823; 422/55; 422/56; 422/58; 422/60; 422/70
(58) Field of Search ................................. 435/7.1, 7.94, 435/287.7, 970; 436/514, 518, 530, 541, 161, 16, 810, 823; 422/55–60, 70

(56) References Cited

U.S. PATENT DOCUMENTS 4,303,409 A * 12/1981 Ogawa et al. ................ 436/93
5,500,375 A * 3/1996 Lee-Own et al. ........... 436/514
5,877,028 A   3/1999 Chandler et al.

FOREIGN PATENT DOCUMENTS

EP          0291194      * 4/1988
WO      WO 01/27627       4/2001

OTHER PUBLICATIONS

Scientific Products General Catalog. p. 946. 1991.*

* cited by examiner

Primary Examiner—Bao-Thuy L. Nguyen
(74) Attorney, Agent, or Firm—Walter A. Hackler; Bella Fishman

(57) ABSTRACT

A lateral flow immunoassay device includes a membrane strip for enabling capillary migration of a sample therealong with a labeled reagent disposed on the membrane. The label reagent is formulated for suspension in the sample migrating therepast. A captive reagent is immobilized on the strip on a path of sample migration and the captive reagent is formulated to bind to the labeled reagent to form a visible colored site on the strip. An element is provided for changing the strip to a color which enhances visual perception of the colored site.

14 Claims, 1 Drawing Sheet

COLOR CONTRAST SYSTEM FOR LATERAL FLOW IMMUNOASSAY TESTS

The present invention generally relates to solid phase immunoassay test devices whether the sandwich or competition type for providing sensitive detection of an analyte in a biological fluid sample and is more particularly directed to a colored contrast system therefore. Solid phase immunoassay test devices incorporate a solid support to which one member of the ligand-receptor pair, usually an antibody, antigen, or hapten is bond.

Lateral flow immunoassay tests in typical use today, generally include a porous component of nitrocellulose membrane, as the solid, with specific reagent applied onto specific zones therein.

An upstream zone usually includes a specific binding reagent for the analyte being tested, conjugated to a visible label such as a gold colloid or colored latex particle. The labeled reagent is formulated to facilitate its released from the membrane after the sample is applied to the test strip.

In typical competition assays, a sample containing analyte is introduced to a sample area of the test strip. Migration of the sample, caused by the capillary wicking within the porous membrane, re-suspends the labeled reagent from its stationary position on the strip. As the reagent mixture migrates along the strip it is brought into contact with the immobilized capture reagent. If the analyte is present in the sample, binding to the labeled reagent (Antibody-visual label) will take place during this migration.

If the amount of analyte is enough to exhaust all binding sites on the labeled reagent, binding of the visual label to the capture reagent will not occur. This constitutes a positive result.

If there is no analyte in the sample, the visual label will bind at the capture stripe producing a negative result seen as a colored band or strips.

For the most part, these tests are interpreted visually by human eye to determine the presence or absence of an analyte (drug). Membranes like nitrocellulose provide a white background to visualize the presence or absence of the colored line or stripe. Presently, white in the only color commercially available for nitrocellulose membrane.

Partial sight, aging, and congenital color deficits can produce changes in perception that reduce the visual effectiveness or certain color combinations.

The present invention provides for lateral flow immunoassay device utilizing complementary colors to provide better contrast for visual perception of test results.

SUMMARY OF THE INVENTION

A lateral flow immunoassay device in accordance with the present invention generally includes a porous strip for enabling capillary migration of a fluid sample therealong. A labeled reagent is disposed on the stripe with the label reagent being formulated for suspension in the sample migrating therepast. A captive reagent is immobilized on the strip in a path of the sample migration with the captive reagent being formulated to bind to the labeled reagent to form a visual colored site on the strip.

Also included are means for providing a complimentary color background for the colored site in order to increase visual perception of the colored site.

In one embodiment of the present invention, the means for providing a complimentary color background comprises a dye incorporated into the porous strip. In another embodiment of the present invention a means for providing a complementary color background comprises a transparent colored film disposed over the porous strip. The film may be in direct contact with the strip by adhesive or suspended over the strip in close proximity therewith with minimal or no contact with the strip.

When a white porous nitrocellulose membrane is used for the porous strip, the means in accordance with the present invention is, in effect an element for changing the white strip to a color which enhances a visual perception of the colored site.

The nitrocellulore membrane may be formed on a Mylar backing, as is well known in the art. In the case of the present invention this Mylar backing may be an optically clear yellow Mylar and membrane viewed through the Mylar backing as will be discussed hereinafter.

In the embodiment in which a film is utilized, the latter may be laminated or adhered to the porous strip or spaced apart therefrom as hereinabove noted.

More specifically, when the colored site is blue, the complementary color background may be selected from a group consisting of yellow, yellow-orange and orange.

Alternative complimentary color combination that may be utilized such as a green background when the colored site is red.

The present also provides for an improvement in existing lateral flow immunoassay devices having a strip for enabling capillary migration of a fluid sample therethrough, a label, reagent disposed on the strip and formulated for suspension in the sample migrating therepast, and a captive agent immobilized on the strip in a path of sample migration and formulated to bind with the label reagent to form a visible site on the strip. The improvement comprises a colored background for enhancing the color perception of the colored site which, may be, for example, a dye incorporated into the strip or a transparent film of a selected background color either directly laminated to the nitrocellulose strip by pressure sensitive adhesive or suspended barely above the strip with minimal or no contract with the strip, facilitated by a die-cut thin plastic carrier, or the like.

A method in accordance with the present invention for enhancing visual perception of a colored site in a immunoassay device includes dying the strip a color which is complimentary to the colored site produced by binding of the labeled reagent and the capture reagent or the step of providing a transparent film having a color which is complimentary to the colored site.

BRIEF DESCRIPTION OF THE DRAWINGS

The advantages and features of the present invention will be better understood by the following description when considered in conjunction with the accompanying drawings in which.

DETAILED DESCRIPTION

Figure 1:
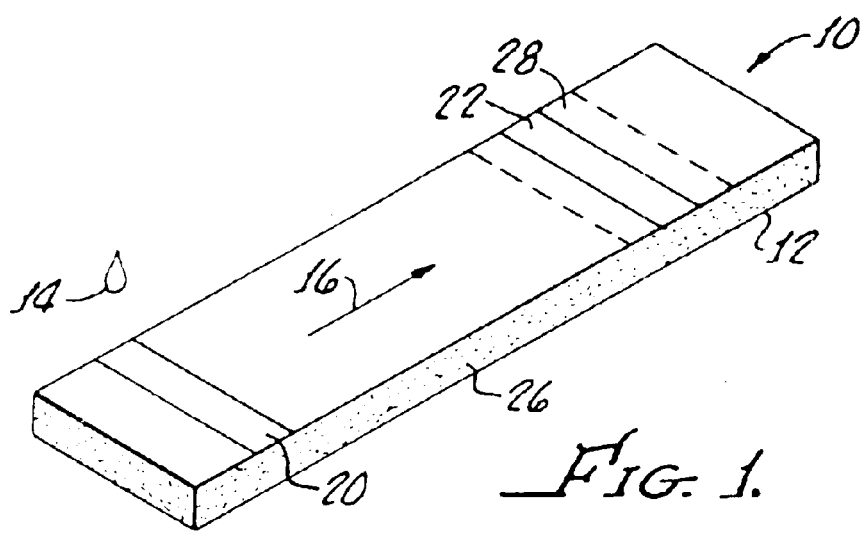
FIG. 1 is a perspective view of a lateral immunoassay in accordance with the present invention generally showing a porous strip, a label reagent disposed on the strip along with a captive reagent immobilized on the strip and a representation of dye present in the strip for providing a color background as will be hereinafter described in greater detail.

With reference to FIG. 1, there is shown a lateral flow immunoassay device 10 in accordance with the present invention which generally includes a porous strip 12, which typically is a nitrocellulose membrane or the like, which enables capillary migration of a fluid sample 14 therealong as represented by the arrow 16 after the deposition of the sample 14 onto the strip 12. The deposition preferably occurs on an area 20 of the strip where a labeled reagent is disposed. The labeled reagent is formulated, as is well known in the art, for suspension in the sample migrating therepast. A captive reagent is immobilized on the strip at a second zone 22 and formulated to bind to the labeled reagent to form a visible site on the strip.

In the embodiment 10 shown in FIG. 1, a dye 26, which is preferably indelible, is incorporated as an element which acts as a means for providing a complimentary color background for the colored site in order to increase visual perception of the colored site. Complimentary colors are those which appear generally opposite one another on a conventional color wheel which include the primary colors of yellow, blue and red.

Typical labeled reagents, such as, blue latex microparticles conjugated to drug antibody, and captive reagents such as, immobilized drug conjugates, result in a blue site. Complementary colors for blue are yellow and orange which are "warm" colors that can optically move the subject, i.e., the blue colored site to the foreground.

As hereinabove noted color compliments are color opposites. They are opposite each other on the color wheel, for example, blue is opposite orange and yellow. These colors are in extreme contrast to each other while making each more intense, for example, a bright orange or yellow background will highlight and make blue more vibrant.

This is an advantage to the visual interpretation of a lateral flow test when the signal to be interpreted becomes faint to the eye due to the quantity of analyte. In competitive assays, low amounts of analyte, under the proposed cut-off of the test, will weaken the visual signal to the point of producing a false positive. The present invention provides for a color contrast system that makes the color signal easier to see. In typical "sandwich" assays in which a colored line indicates a positive sample, the color contrast system in accordance with the present invention helps prevent false negatives particularly in persons with color vision defects.

While a permanent dye 26 may be utilized in accordance with the present invention, it should be appreciated that chemical components may be added to the strip which in fact cause a color background to be developed at the same time as binding of the labeling reagent in the captive reagent to form the colored site. For example, an anti BSA captive zone 28 may be provided under the capture zone 22, and broader thereof, and yellow latex microparticles introduced that have immobilized BSA on the surface with the blue latex microparticulates. As the sample runs, the yellow microparticulates will stop at the BSA captive zone 28, making it yellow, and if a drug was not present the blue microparticulates will stop at the captive zone 22.

Figure 2:
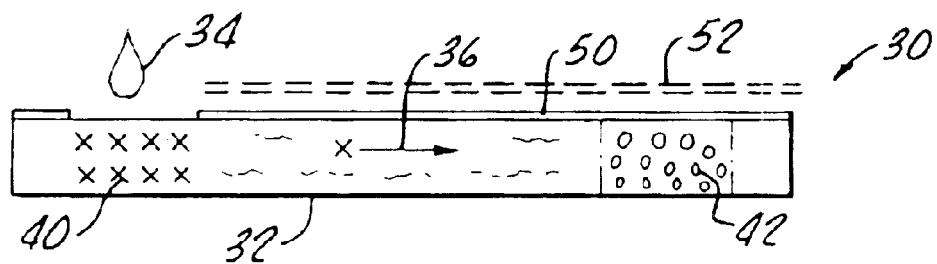
FIG. 2 is a cross-sectional view of another embodiment of the present invention showing a porous strip and representations of a labeled reagent disposed on the strip, a captive reagent immobilized on the strip and a transparent film for providing a complimentary background.

Alternatively, as shown in FIG. 2 a second embodiment 30 of a lateral flow immunoassay device in accordance with the present invention, includes a porous strip 32 for enabling a sample to migrate therealong by capillary action as indicated by the arrow 36.

A labeled reagent 40 is disposed on the membrane and formulated as hereinabove noted for suspension in the sample 34 for migrating therepast. A captive reagent 42 is immobilized in the strip 32 in the path of sample migration and formulated to bind with the label reagent to form a visible colored site on the strip.

In the embodiment 30 the strip 32 may be a white porous membrane and a transparent film 50 of a selected color is disposed over the membrane strip 32. In order to provide a unitary device 30, the film 50 may be laminated to the membrane strip 32.

Alternatively, the film 50, which may be in the form of a plastic carrier or encasement 52, may be suspended above the strip 32 and include a transparent pigment for allowing light and the underlining test strip 32 to be visualized.

Figure 3:
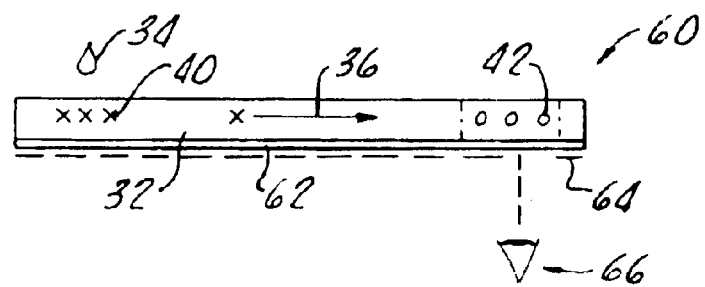
FIG. 3 is an alternative embodiment of the present invention utilizing a nitrocellulose membrane on a colored backing.

An alternative embodiment 60 of the present invention is shown in FIG. 3. Common references characters shown in FIG. 3 correspond to identical or similar reference characters shown in FIGS. 1-2.

The embodiment 60 includes the porus membrane 32 disposed on a transparent colored backing 62 preferably yellow Mylar. Alternatively a clear Mylar backing may be used with a transparent colored film 64, thereon as indicated in dashed line in FIG. 3. In this embodiment, the membrane 32 is viewed through the Mylar 62 as indicated by the icon 66.

EXPERIMENTAL RESULTS

Lateral flow test strips were challenged with various levels of analytes and specimens. The levels were focused around the detection limits of the test device. The blue latex colored particles were used for the test. Two sets of identical test strips were challenged with the specimens. One set of the test strips where covered with a yellow Mylar strip. Multiple individuals made visual reads of the strips and the readers commented on the ease of reading strips when the yellow film covered the test strip which enhanced their ability to interpret the presence or absence of the blue line result.

Although there has been hereinabove described a lateral flow immunoassay device in accordance with the present invention utilizing a specific complimentary colors of yellow and blue, it should be appreciated that the invention is not limited thereto but further incorporates the use of any sets of complimentary colors for enhancing visual equity of test results. Accordingly, any and all modifications, variations, or equivalent arrangements which may occur to those skilled in the art should be considered to be within the scope of the invention as defined in the appended claims.

What is claimed is:

1. A lateral flow immunoassay device comprising:
    a porous strip for enabling capillary migration of a fluid sample therealong;
    a labeled reagent disposed on the strip, said labeled reagent being formulated for suspension in the sample migrating therepast;
    a captive reagent immobilized on strip in a path of sample migration, said captive reagent being formulated to bind to said labeled reagent to form a visible colored site on the strip; and
    means for providing a complimentary color background for the colored site in order to increase visual perception of the colored site, said means comprising a transparent colored film disposed over said porous strip.

2. The device according to claim 1 wherein the film is suspended above said porous strip.

3. The device according to claim 1 wherein the film is laminated to said porous strip.

4. The device according to any one of claims 1 through 3 wherein the colored site is blue and the complimentary color background is selected from a group consisting of yellow, yellow-orange and orange.

5. The device according to any one of claims 1 through 2 wherein the colored site is red and the complimentary color background is selected from a group consisting of green, light green, fluorescent green and lime green.

6. A lateral flow immunoassay device comprising:

a white porous nitrocellulose membrane for enabling capillary migration of a fluid sample therealong;

a labeled reagent disposed on the strip, said labeled reagent being formulated for suspension in the sample migrating therepast;

a captive reagent immobilized on the strip in a path of sample migration, said captive reagent being formulated to bind to said labeled reagent to form a visible colored site on the strip; and an element for changing the white strip to a color which enhances visual perception of said colored site, said element comprising a colored transparent film adhering to said test strip.

7. The device according to claim 6 wherein the element comprises a dye incorporated into the membrane.

8. The device according to claim 7 wherein said transparent film is laminated to the membrane.

9. The device according to claim 6 wherein said element further comprises a colored backing for supporting the membrane.

10. The device according to claim 6 wherein said element further comprises a clear backing for supporting the membrane and the colored transparent film is adhered to said clear backing.

11. The device according to any one of claims 6 through 10 wherein the colored site is blue and the enhancing color is selected from a group consisting of yellow, yellow-orange and orange.

12. The device according to any one of claims 6 through 10 wherein the colored site is red and the enhancing color is selected from a group consisting of green, light green, fluorescent green and lime green.

13. An improvement in a lateral flow immunoassay device having a strip for enabling capillary migration of a fluid sample therealong, a labeled reagent disposed on the strip and formulated for suspension in the sample migrating therepast and a captive reagent immobilized on the strip in a path of sample migration and formulated to bind to said labeled reagent to form a visible colored site on said strip, said improving comprising a color background for enhancing visual perception of said colored site, wherein said colored site is blue and said colored background is yellow or said colored site is red and said colored background is green.

14. The improvement according to claim 13 wherein said colored background further comprises a transparent film disposed over said strip.

* * * * *

UNITED STATES PATENT AND TRADEMARK OFFICE
CERTIFICATE OF CORRECTION

PATENT NO. : 6,818,456 B2  Page 1 of 1
APPLICATION NO. : 09/910198
DATED : November 16, 2004
INVENTOR(S) : Steven P. Sidwell and Steven S. Bachand It is certified that error appears in the above-identified patent and that said Letters Patent is hereby corrected as shown below:

On the Title page of the patent:

(12) Change "Sidewell" to -- Sidwell --.

(75) Inventors : Change "Sidewell" to -- Sidwell --.

Signed and Sealed this

Twelfth Day of June, 2007

JON W. DUDAS
*Director of the United States Patent and Trademark Office*